United States Patent [19]

Sweeney et al.

[11] Patent Number: 5,746,726
[45] Date of Patent: May 5, 1998

[54] SHIELDED NEEDLE ASSEMBLY

[75] Inventors: Niall Sweeney; Adriano Morigi, both of Rutherford; Sandor Gyure, West Orange, all of N.J.

[73] Assignee: Becton, Dickinson and Company, Franklin Lakes, N.J.

[21] Appl. No.: 702,083

[22] Filed: Aug. 23, 1996

[51] Int. Cl.$^6$ .................................................. A61M 5/32
[52] U.S. Cl. .................................... 604/263; 604/192
[58] Field of Search ................................. 604/192, 110, 604/198, 187, 263

[56] References Cited

U.S. PATENT DOCUMENTS

| | | | |
|---|---|---|---|
| 4,664,259 | 5/1987 | Landis | 604/192 |
| 4,886,503 | 12/1989 | Miller | 604/263 X |
| 4,976,699 | 12/1990 | Gold | 604/192 |
| 4,982,842 | 1/1991 | Hollister | 206/365 |
| 5,207,653 | 5/1993 | Janjua et al. | 604/192 |
| 5,486,163 | 1/1996 | Haynes | 604/263 X |

*Primary Examiner*—John D. Yasko
*Attorney, Agent, or Firm*—Arthur D. Dawson

[57] ABSTRACT

A needle assembly includes an elongate needle with a proximal end, a distal end and a passageway therethrough. The assembly has a needle hub with a proximal end, a distal end and an outside surface. The hub has an axial opening therethrough to receive and hold the proximal end of the needle with the distal end of the needle projecting distally axially. The assembly includes an elongate shield with an open proximal end, a closed distal end and a sidewall that has an elongate opening on one side extending from the closed end to the open end. The shield of the invention is movable between an open position, in which the needle is exposed for use by passage through the elongate opening and a latched position, in which the shield is substantially prevented from movement to the open position and the shield substantially obstructs access to the needle. The assembly has a hinge including a mount for holding the shield onto the needle hub with the shield movable between the open position and the latched position by an off-axis pivotal movement about the hinge. There is a latch for releasably latching the shield that includes at least one hook on the proximal end of the shield adjacent the elongate opening and at least one lug on the mount. The lug includes a deflectable projection disposed so that when the projection is deflected toward the axis of the assembly, the hook and the lug are disengaged.

6 Claims, 13 Drawing Sheets

SHIELDED NEEDLE ASSEMBLY

FIELD OF THE INVENTION

The present invention relates to a protective shield for a needle and more particularly to a shielded needle assembly that includes the hub of the needle, and allows use of the needle on a syringe, needle holder or other fluid handling device.

DESCRIPTION OF RELATED INFORMATION

In the medical arts, sharp pointed needles are used in many procedures. Devices having sharp pointed needles are used for administering fluids to patients either directly or into intravenous apparatus, and in various blood drawing applications either with syringes or with specialized holders for filling evacuated tubes. Since needles are so widely used in medical procedures, many people are potentially exposed to needles in the routine course of their work. These needle exposures are not limited only to the practitioners directly involved in patient treatment, but also include support workers all through the hospital. These support workers include hospital pharmacy technicians, who prepare dosages, and hospital service personnel, such as laundry, housekeeping, etc.

Needle exposure problems are not just limited needle sticks from already used needles. Hospital pharmacy workers often prepare syringes with doses of costly medications, recap the syringe, and transport the syringe with the dose to the patient. If the pharmacy worker inadvertently sticks himself or damages the needle, the syringe and the dose is likely rendered unusable. Exposure to blood borne pathogens should be a recognized hazard by anyone associated with the medical arts. As a result of this recognition, numerous protocols for use of needles have been developed and are widely practiced. The problem of transmission of blood borne pathogens not only exists for the physician, nurse or phlebotomist using the needles, but also for support workers all through the hospital.

The use protocols generally dictate in detail when and how a needle is used and how it should be disposed of. The problem with many protocols for handling needles is that the protocols often require users to perform additional steps in a procedure. With the press of time and simple carelessness, certain practices regarding handling of used needles are sometimes disregarded and injuries still occur. The medical device industry has responded to the problem by producing a wide variety of sharps collectors, needle shielding devices and the like to assist practitioners in their need to reduce the occurrence of needle injuries.

Many devices have been developed for shielding needles after use to avoid exposing people to used needles. A representative listing of many of these devices is found in U.S. Pat. No. 4,982,842 to Hollister et al. Hollister et al. discloses a stand alone adapter that has a male and female end for mating with a needle assembly and the ejection end of a syringe. The device of Hollister et al. includes a housing mounted to the adapter which may be pivoted to a position in alignment with the needle for enveloping the needle and locking the needle to retain it in the housing. The Hollister et al. device increases the unusable or "dead-space" volume of the device on which the adapter is mounted, and requires an additional part that increases the projection of the needle hub. Also, if bevel position is important to the intended use of the needle, the Hollister et al. invention must be carefully aligned with the needle point when mounted.

U.S. Pat. No. 5,207,653 to Janjua et al. discloses a needle cap with a longitudinal slit having a width greater than the width of a needle. According to Janjua et al., the needle cap is adapted to be pivotally connected with the needle and hub piece. Janjua et al. also discloses that the needle cap is usable with a syringe or with a needle holder for fluid collection tubes. The device disclosed by Janjua et al. mounts on the needle hub with a pivot, but since it only pivots in one plane, unless the needle point is precisely oriented with the hub during assembly, the shield may interfere in some applications.

Most of the devices listed in the background of the Hollister et al. patent, the Hollister et al. invention itself and the Janjua et al. invention, attempt to address the recognized need to protect medical and service personnel from needle sticks. There are several recurrent problems in varying degrees with these devices. Many of these previous devices are somewhat complex, hence are significantly more costly than an unprotected device. Many of these previous devices also increase the complexity or increase the difficulty of performing a procedure. Some others of the previous devices are so procedure specific that they preclude use of the device in certain other procedures. For these and similar reasons most of the devices disclosed in the Hollister et al. background have never been successfully commercialized.

Blood drawing is one application that is particularly sensitive to needle point orientation. Most phlebotomists carefully align a needle point with the beveled face away from the skin so that the needle point placement may be precisely controlled. A needle assembly as disclosed in Janjua et al. would either sometimes be clumsy to use because the shield would sometimes be in the way or, alternatively, more expensive because of the need to carefully orient the point during manufacture. Additionally, in the Janjua et al. patent, while there is a recognition of the need to secure the cap in the closed position over the needle, all of the solutions proposed require additional steps such as securing the cap with an adhesive or twisting the cap.

Although there already are many shielded needle devices, there is still a need for a shielded needle device that is easily manufactured, applicable to many types of fluid handling devices, as well as simple and intuitive to use. Additionally, the needle device should not interfere with normal practices of use. Such a device is described below.

SUMMARY OF THE INVENTION

A needle assembly of the present invention includes an elongate needle with a proximal end, a distal end and a passageway therethrough. The assembly has a needle hub with a proximal end, a distal end and an outside surface. The hub has an axial opening therethrough to receive and hold the needle at the distal end of the needle hub with the distal end of the needle projecting distally axially. The proximal end of the needle hub further includes a fitting for releasably mounting the needle hub on a fluid handling device. The assembly further includes an elongate shield with an open proximal end, a closed distal end and a sidewall that has an elongate opening on one side. The shield of the invention is movable between an open position, in which the distal end of the needle is exposed for use by passage through the elongate opening and a latched closed position, in which the shield is substantially prevented from movement to the open position and the shield substantially obstructs access to the needle. The assembly has a hinge including a mount for holding the shield onto the needle hub. The mount is sized and shaped to receive at least a portion of the needle hub and to retain the mount on the needle hub. The shield is movable between the open position and the latched position by an off-axis pivotal movement about the hinge. There is a latch for releasably latching the shield to the mount. The latch includes at least one hook on the proximal end of the shield adjacent to the elongate opening and at least one lug on the mount. The hook and the lug are disposed to engage releasably when the shield is moved to the latched position. The lug includes a deflectable projection disposed so that when the projection is deflected, the hook and the lug are disengaged and the shield is pivotable about the hinge to its open position.

The shielded needle assembly of the invention allows a practitioner to move the shield between the open position to expose the needle and the latched position to cover the needle without either having to use two hands or without having to position a hand in close proximity to the point of the needle. The shielded assembly of the invention is particularly useful for applications where a syringe is prepared with a dose of a medication, then reshielded and transported to the patient for administration of the medication. The practitioner can easily close and latch the shield to protect personnel and the needle during transport to the patient, open the shield to administer the dose, and once the dose is administered, close and latch the shield for appropriate disposal of the syringe and needle assembly. Since the shielded needle assembly of the invention includes the needle hub, the assembly does not increase the dead-space volume of the syringe/needle combination above the dead-space volume of a standard unshielded needle assembly. In treatments with costly medicaments, any increase in dead-space volume results in a costly waste of the medicament.

DETAILED DESCRIPTION

While this invention is satisfied by embodiments in many different forms, there are shown in the drawings and herein described in detail, preferred embodiments of the invention with the understanding that the present disclosure is to be considered exemplary of the principles of the invention and is not intended to limit the invention to the embodiments illustrated. The scope of the invention is measured by the appended claims and their equivalents.

Figure 1:
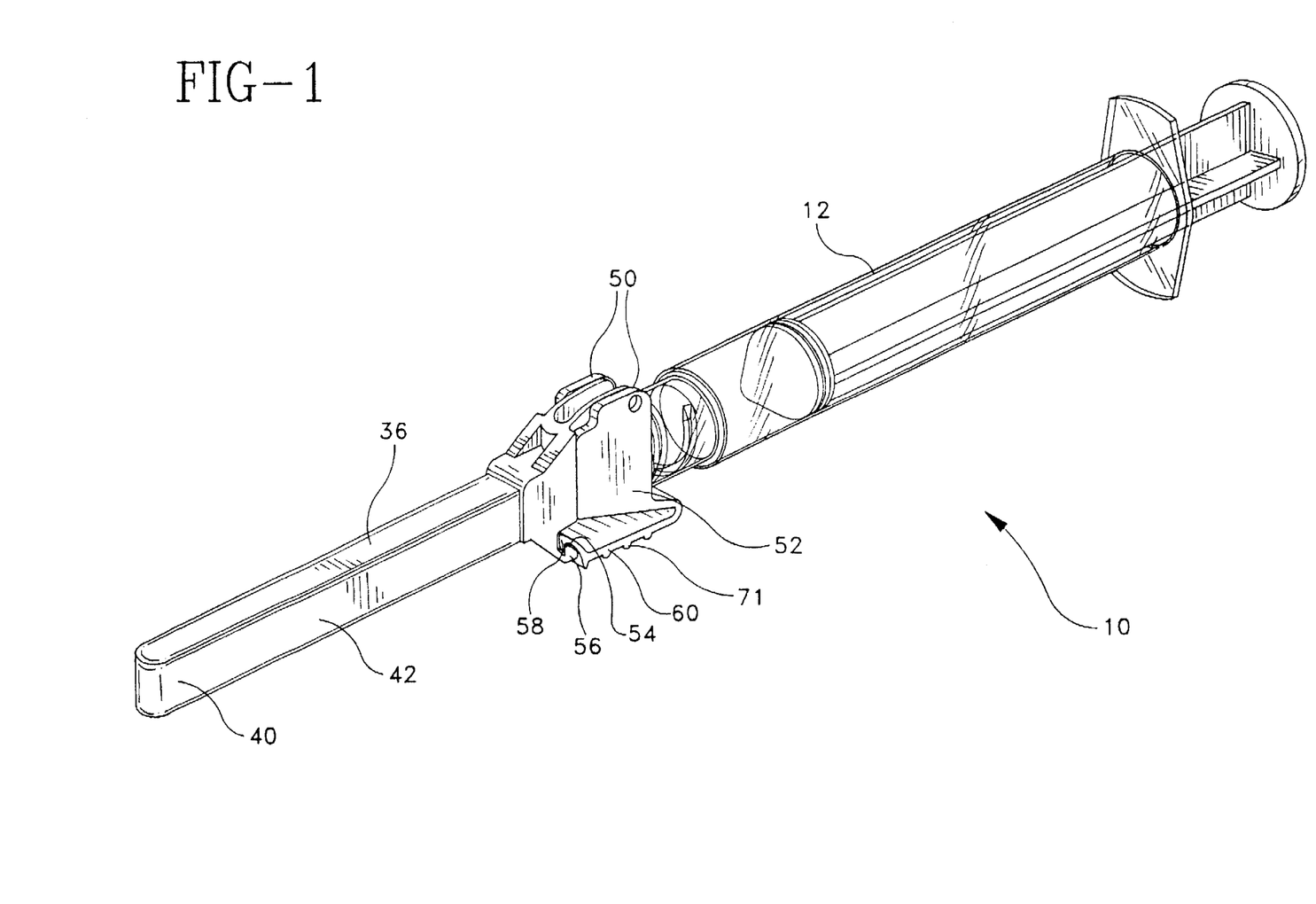
FIG. 1 is a perspective view of a preferred needle assembly of the present invention with the shield in the latched position and mounted on a syringe.
Figure 2:
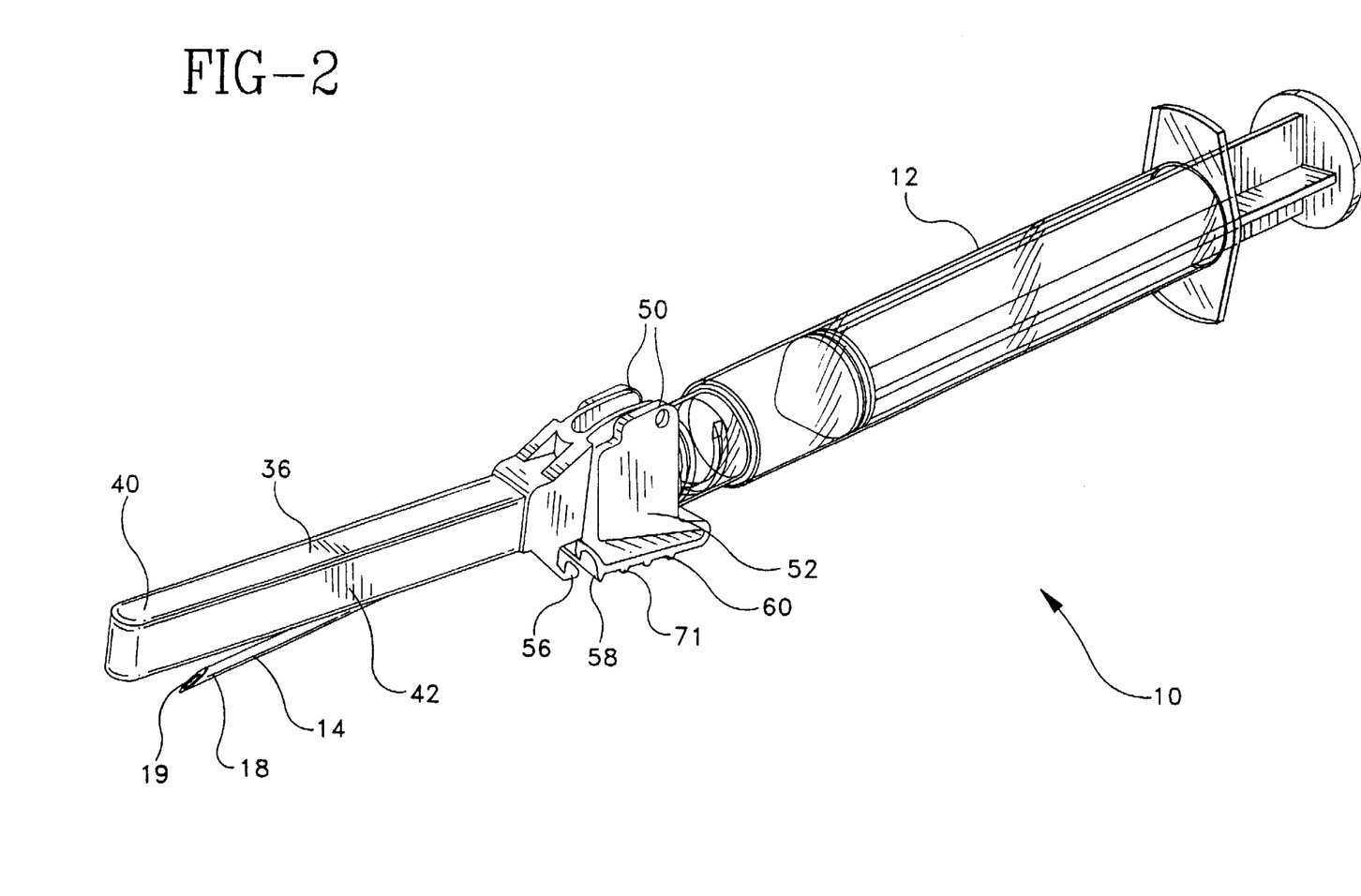
FIG. 2 is a perspective view of the assembly of FIG. 1 with the shield unlatched and partially opened.
Figure 3:
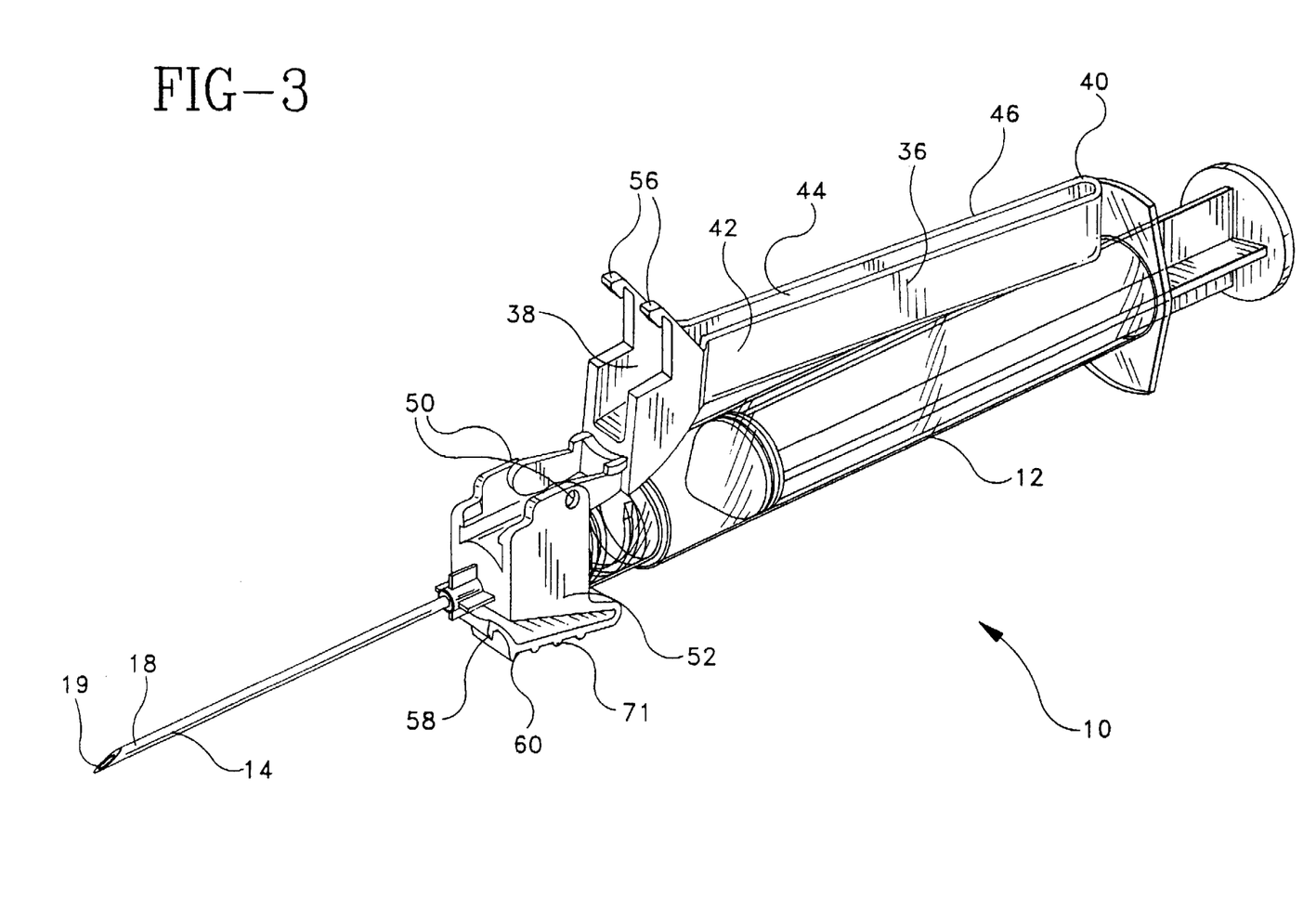
FIG. 3 is a perspective view of the assembly of FIG. 1 with the shield fully opened.
Figure 4:
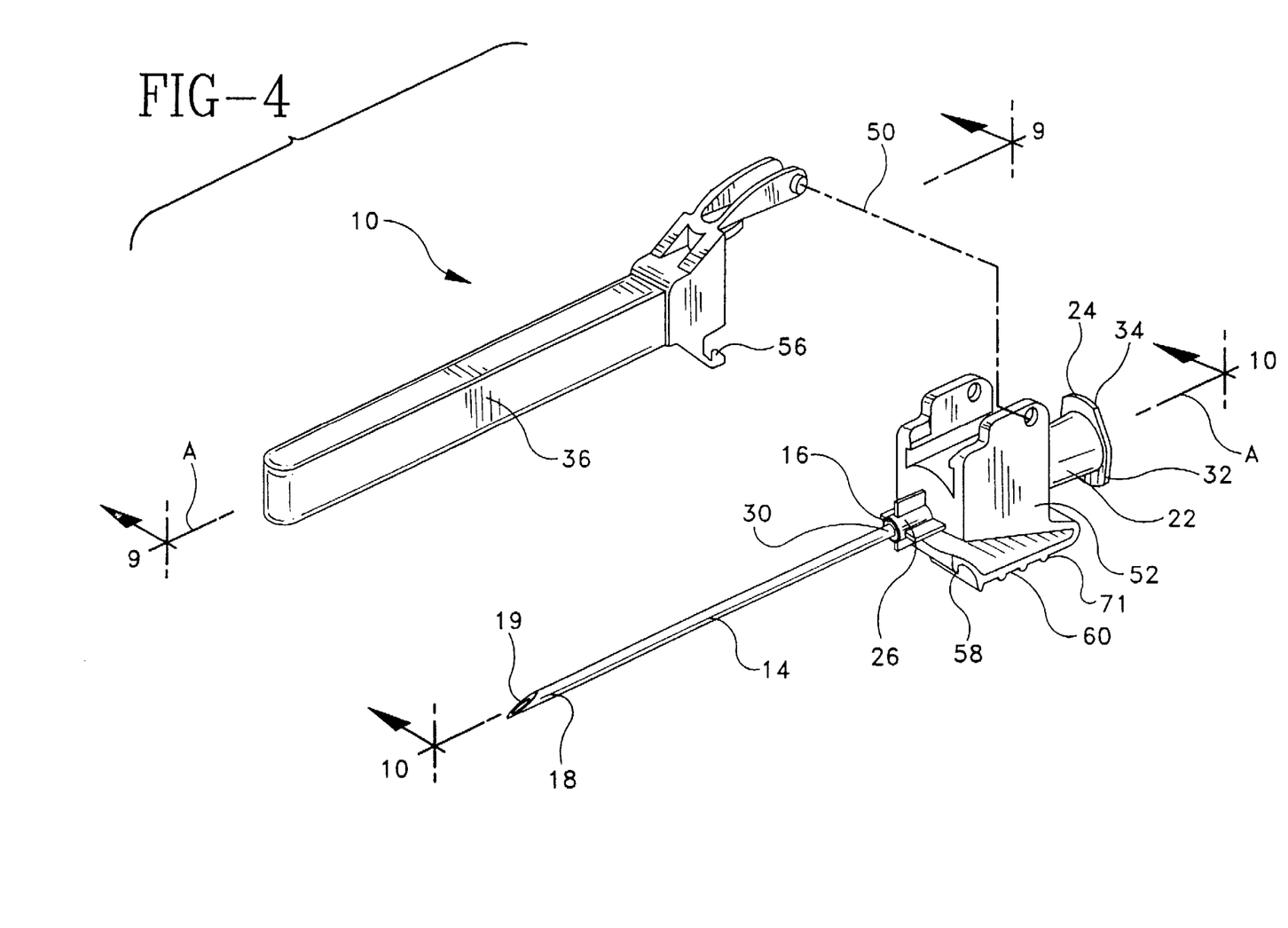
FIG. 4 is a partially exploded perspective view of the assembly of FIG. 1.
Figure 5:
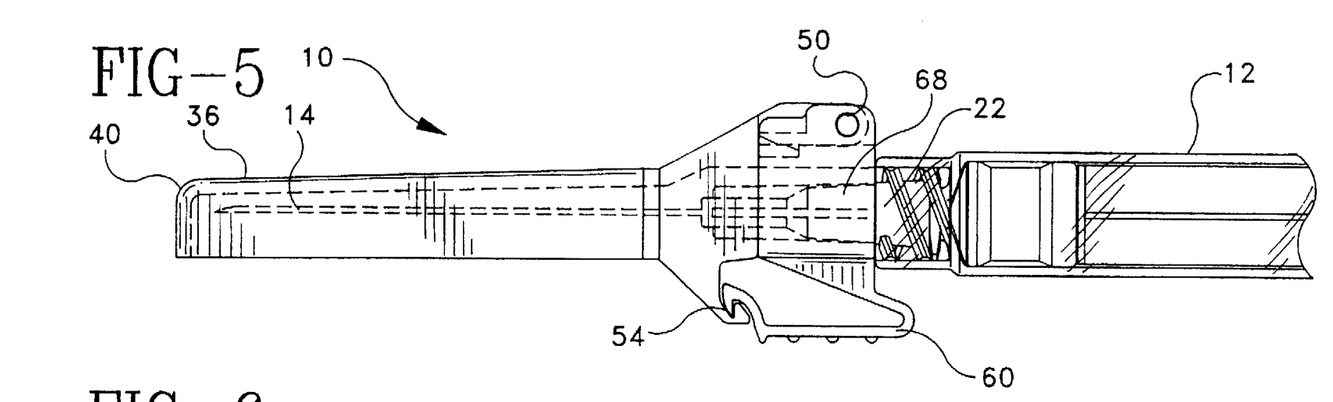
FIG. 5 is a schematic partial side elevation of the assembly of FIG. 1.
Figure 6:
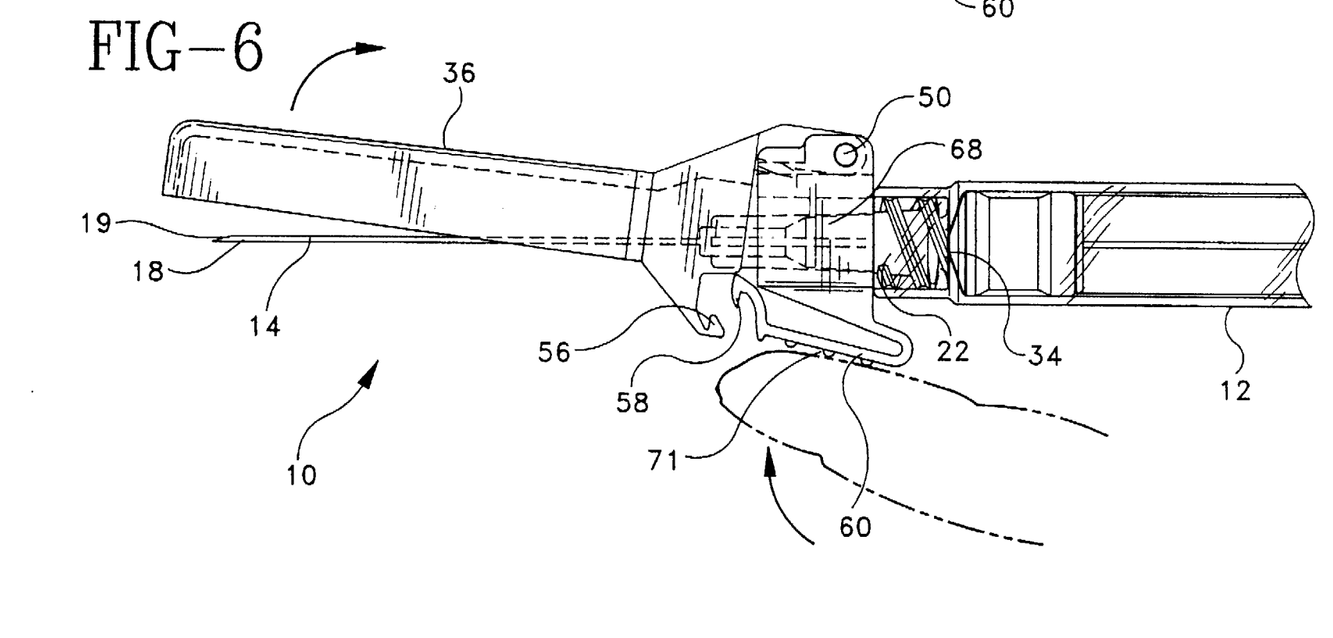
FIG. 6 is a schematic partial side elevation of the assembly of FIG. 1 illustrating operation of the latch, analogous to FIG. 2.
Figure 7:
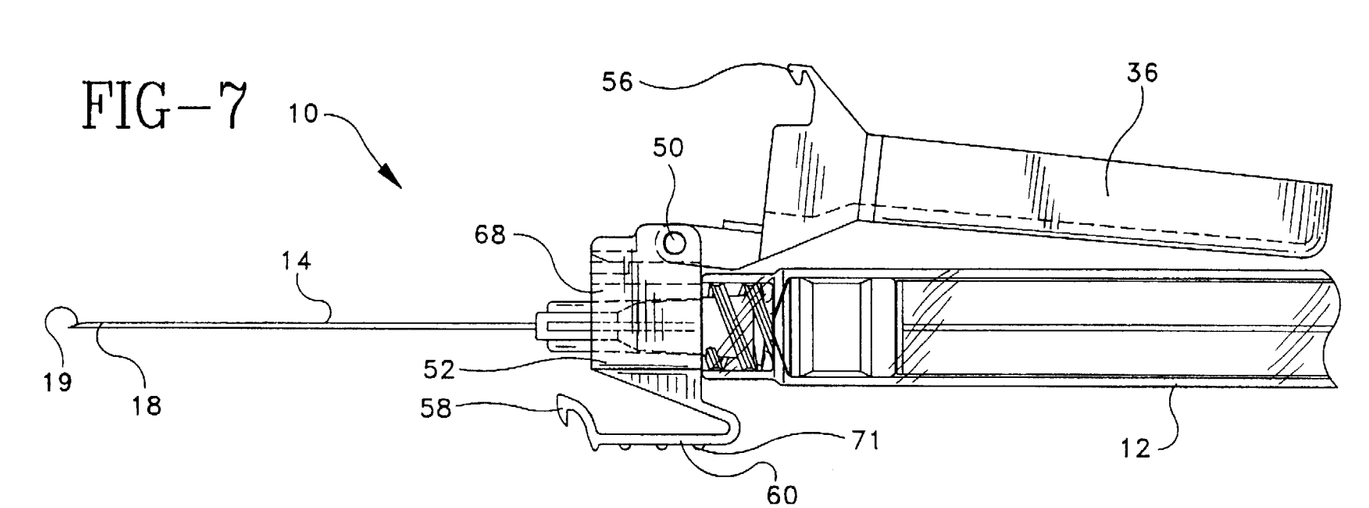
FIG. 7 is a schematic partial side elevation of the assembly of FIG. 1, analogous to FIG. 3.
Figure 8:
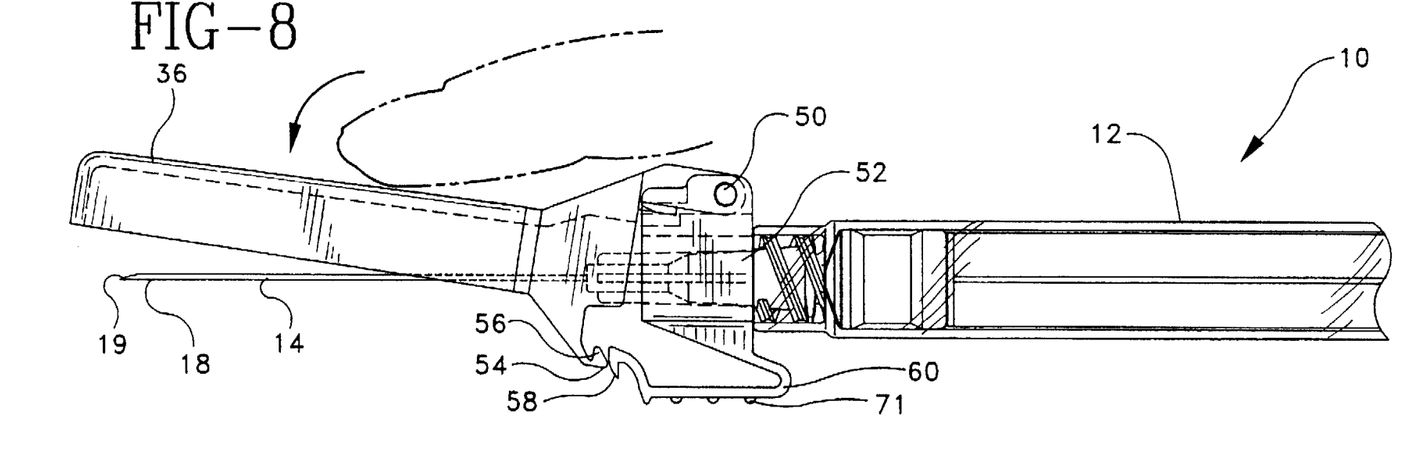
FIG. 8 is a schematic partial side elevation of the assembly of FIG. 1, illustrating return of the shield toward the latched position.
Figure 9:
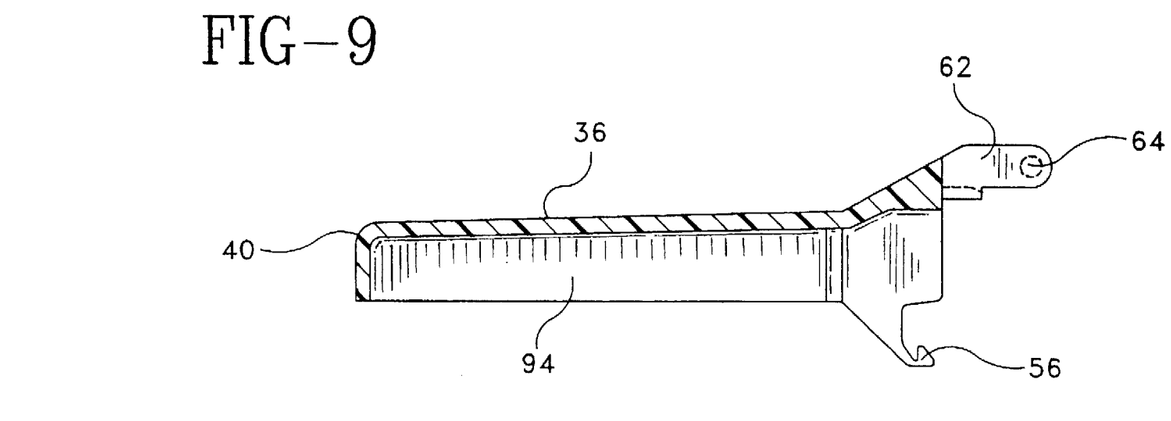
FIG. 9 is a partial cross-sectional view of the shield of the invention from FIG. 4, taken along the line 9—9.
Figure 10:
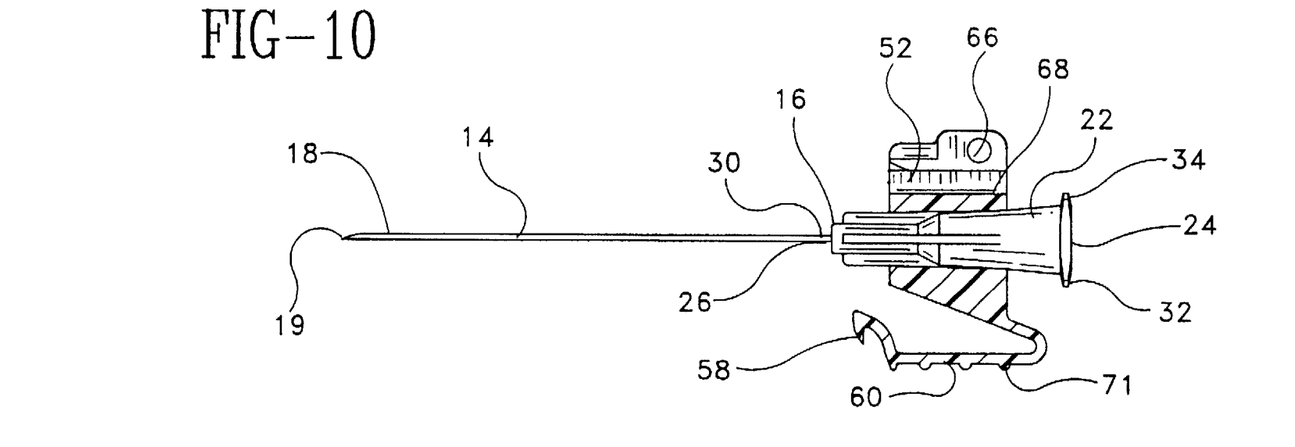
FIG. 10 is a partial cross sectional view of the needle, needle hub and mount of the invention from FIG. 4, taken along the line 10—10.
Figure 11:
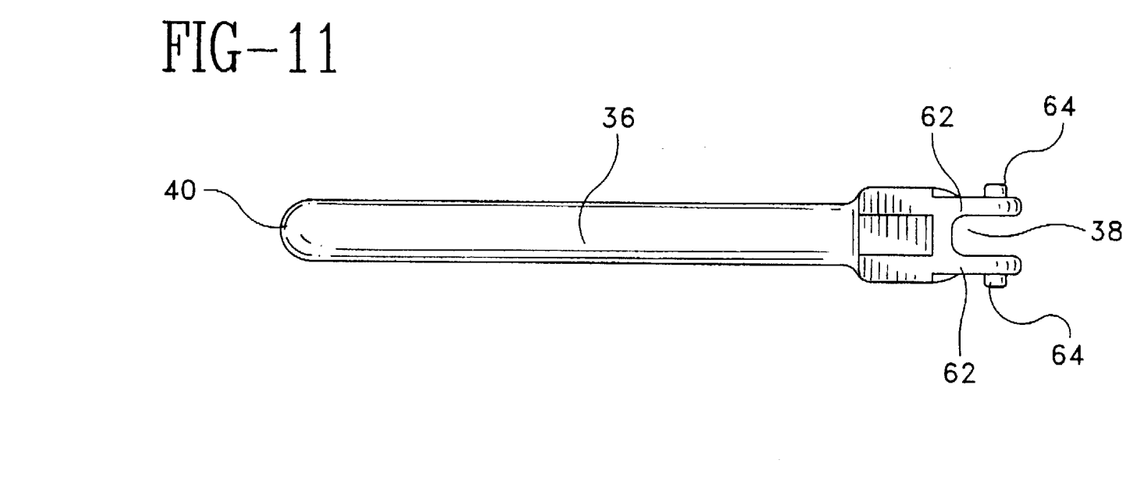
FIG. 11 is a top plan view of the shield of the invention from FIG. 4.
Figure 12:
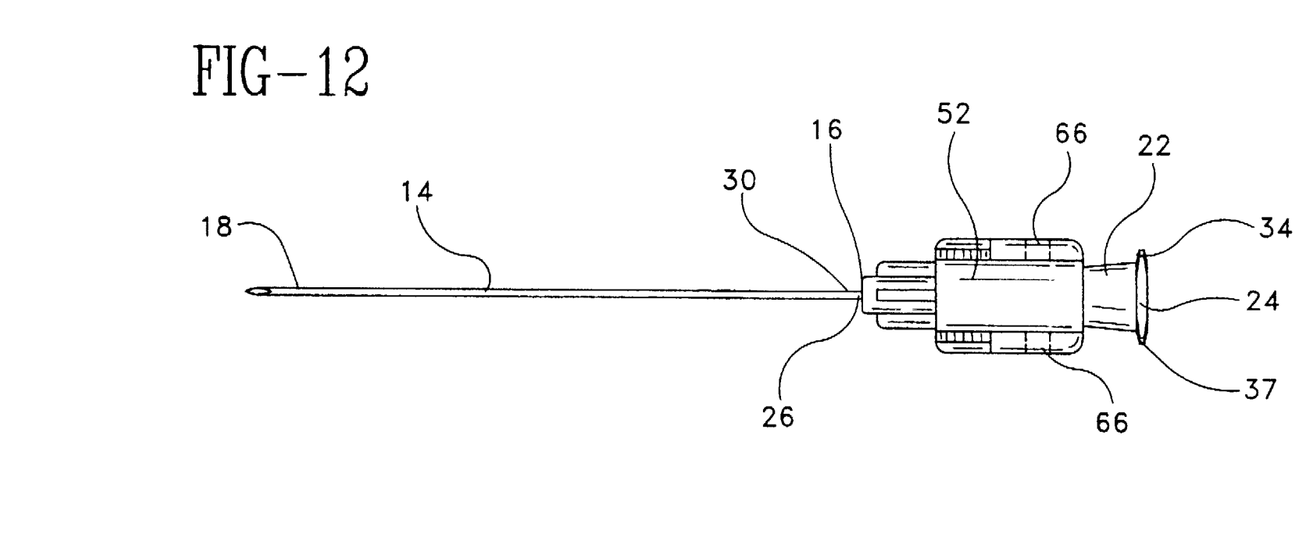
FIG. 12 is a top plan view of the needle, needle hub and mount of the invention from FIG. 4.
Figure 13:
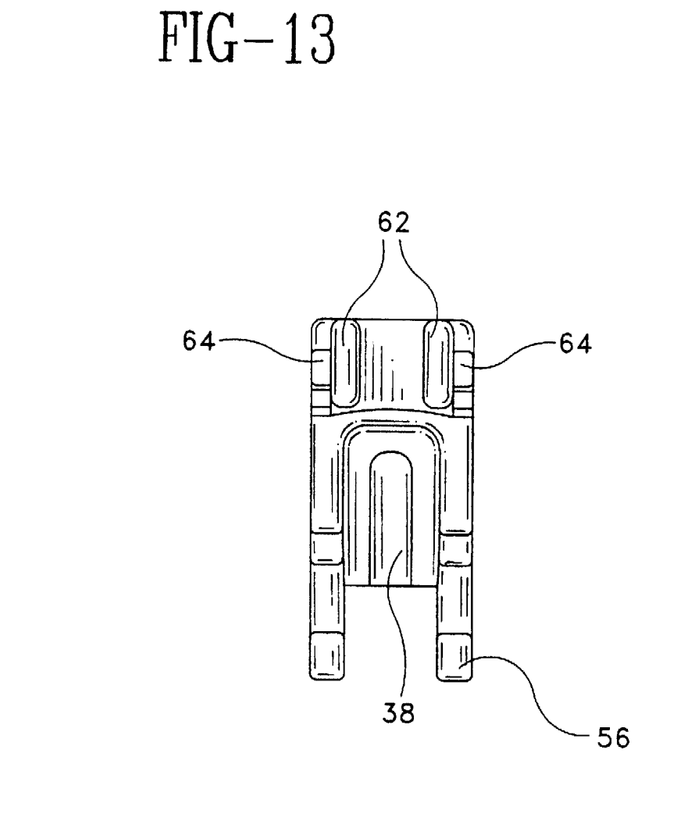
FIG. 13 is a proximal end view of the shield of the invention as seen in FIG. 4.
Figure 14:
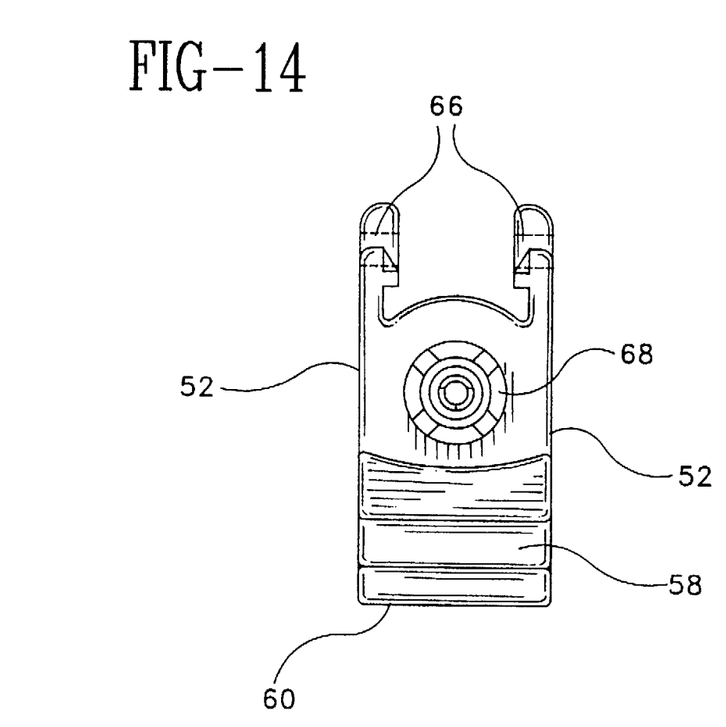
FIG. 14 is a distal end view of the needle, needle hub and mount as seen in FIG. 4.

Referring to FIGS. 1–14, a preferred needle assembly 10 of the present invention, illustrated in FIGS. 1–3 and 5–8 mounted on a syringe 12, includes an elongate needle 14 with a proximal end 16, a distal end 18, preferably having a sharp point with a beveled surface 19, and a passageway 20 therethrough. Assembly 10 has a needle hub 22 with a proximal end 24, a distal end 26 and an outside surface 28. Preferred hub 22 has an axial opening 30 therethrough to receive and to hold the needle at distal end 26 of the needle hub with distal end 18 of the needle projecting distally axially along an axis A. Proximal end 24 of the needle hub further includes a fitting 32 for releasably mounting the needle hub on a fluid handling device, e.g., a female luer fitting 34 for use on syringe 12. The preferred assembly 10 further includes an elongate shield 36 with an open proximal end 38, a distal end 40 and a sidewall 42 that has an elongate opening 44 on a side 46 extending from distal end 40 to open end 38. Distal end 40 is preferably closed. Shield 36 of the invention is movable between an open position, as shown in FIGS. 2, 3, 6, 7 and 8, in which needle 14 is exposed for use by passage through elongate opening 44 and a latched position, as shown in FIGS. 1 and 5, in which shield 36 is substantially prevented from movement to the open position and shield 36 substantially obstructs access to needle 14. Assembly 10 has a hinge 50 including a mount 52 for holding 36 shield onto needle hub 22 with shield 36 movable between the open position and the latched position by an off-axis pivotal movement, best seen in FIGS. 6, 7 and 8, about hinge 50. There is a latch 54 for releasably latching shield 36 to mount 52. Latch 54 includes at least one hook 56, preferably two hooks 56, on proximal end 38 of the shield adjacent elongate opening 44 and at least one lug 58, preferably one lug 58, on mount 52. Hooks 56 and lug 58 are disposed to engage releasably, best seen in FIGS. 1 and 5, when the shield is latched. Lug 58 includes a deflectable projection 60 disposed so that when projection 60 is deflected toward the axis of assembly 10, hooks 56 and lug 58 are disengaged, best seen in FIGS. 2 and 6, and shield 36 is pivotable about hinge 50 to its open position. FIG. 6 illustrates that the shield may be unlatched by a practitioner's finger and partially opened using the deflection of projection 60 to move shield 36 to the partially opened position. Preferably, projection 60 has at least one protuberance 71 on the surface to facilitate a practitioner's finger deflecting projection 60 to release latch 54.

Hinge 50 has two arms 62 projecting proximally from open end 38 of the shield opposite open slot 44. Each arm 62 has a perpendicularly extending peg 64, with mount 52 having two holes 66 therein sized and disposed to receive a peg 64 to form a pivotal hinge 50 and to attach shield 36 to mount 52. Shield 36 is movable about the pivotal hinge 50 between the latched position as shown in FIGS. 1 and 5 and the open position shown in FIGS. 2, 3, 6, 7 and 8.

Mount 52 has an axial opening 68 therethrough that is sized and shaped to receive at least a portion of needle hub 22. Opening 68 includes provisions for retaining needle hub 22 in the mount. In the embodiment illustrated in FIGS. 1–14, hub 22 is fixedly attached in mount 52. Suitable techniques for fixedly attaching hub 22 into the mount include, but are not limited to, an adhesive bond between a wall 69 of the opening and exterior surface 28 of the hub, a mechanical interference fit between the wall of the opening and the hub, a solvent bond between the wall of the opening and the hub, a thermal weld between the wall of the opening and the hub, a mechanical snap-fit and the like.

Figure 15:
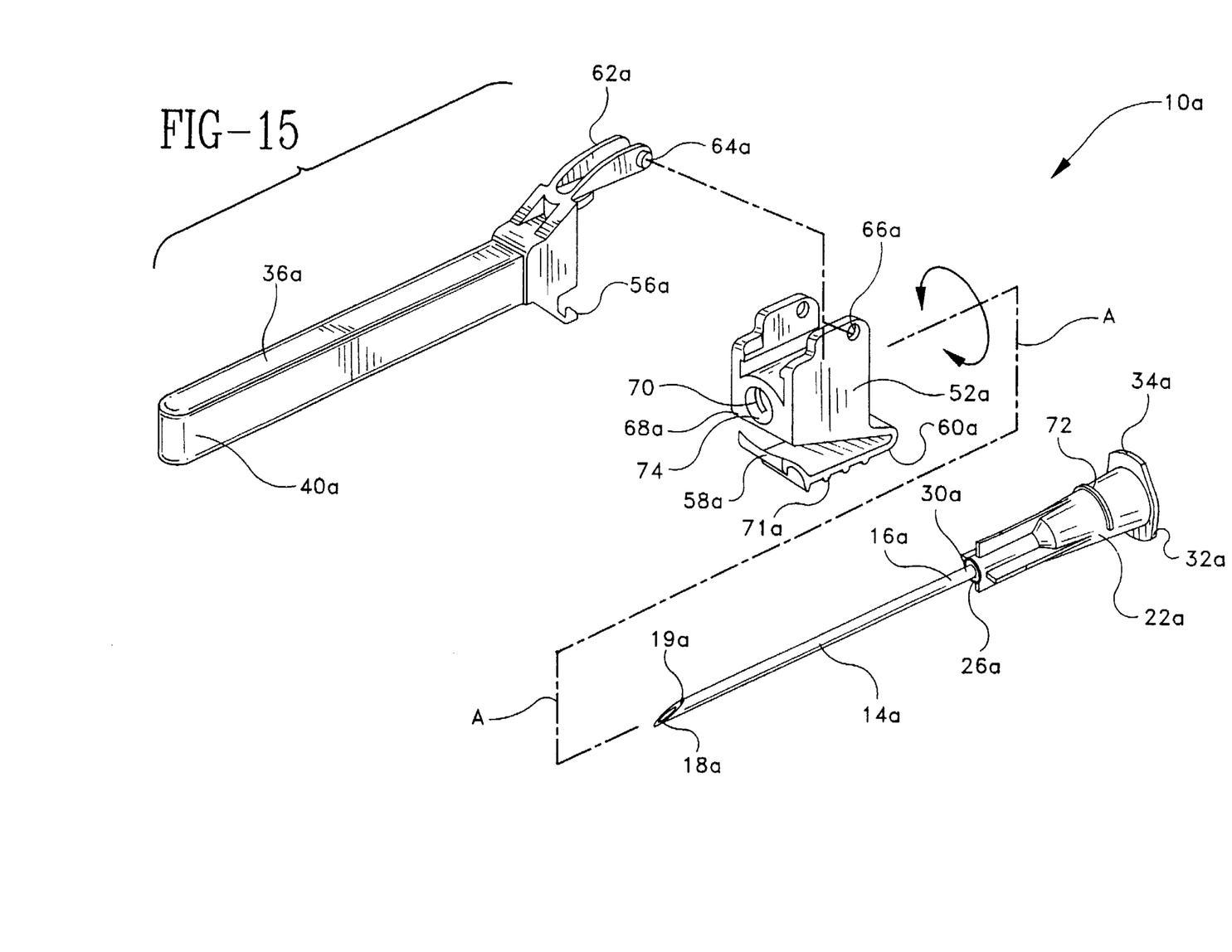
FIG. 15 is an exploded perspective of a more preferred embodiment of the needle assembly of the present invention.
Figure 16:
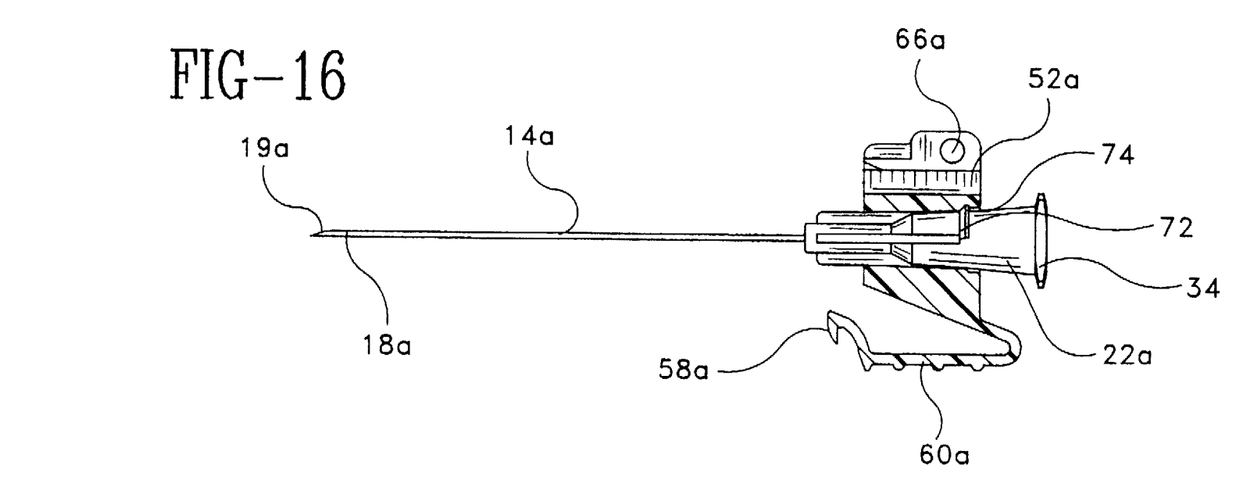
FIG. 16 is a partial cross-sectional view of the assembly of FIG. 15.

A more preferred embodiment of the present invention is shown in FIGS. 15 and 16. In this embodiment, the structure of the needle assembly is substantially similar to the assembly illustrated in FIGS. 1–14. Accordingly, substantially similar components that perform substantially similar functions are numbered identically to those components of the embodiment of FIGS. 1–14 except that a suffix "a" is used to identify those components in FIGS. 15 and 16. Preferred needle assembly 10a of the present invention includes an elongate needle 14a with a proximal end 16a, a distal end 18a and a passageway 20a therethrough. Assembly 10a has a needle hub 22a with a proximal end 24a, a distal end 26a and an outside surface 28a. Hub 22a has an axial opening 30a therethrough to receive and hold proximal end 16a of the needle hub with distal end 18a of the needle projecting distally axially. Proximal end 24a of the needle hub further includes a fitting 32a for releasably mounting the needle hub on a fluid handling device, e.g., a female luer fitting 34a for use on syringe 12. Preferred assembly 10a further includes an elongate shield 36a with an open proximal end 38a, a closed distal end 40a and a sidewall 42a that has an elongate opening 44a on one side 46a extending from closed end 40a to open end 38a. Shield 36a of the invention is movable between an open position in which needle 14a is exposed for use by passage through elongate opening 44a and a latched position in which shield 36a is substantially prevented from movement to the open position and shield 36a substantially obstructs access to needle 14a. Assembly 10a has a hinge 50a including a mount 52a for holding shield 36a onto needle hub 22a with shield 36a movable between the open position and the latched position by an off-axis pivotal movement about hinge 50a. There is a latch 54a for releasably latching shield 36a to mount 52a. Latch 54a includes at least one hook 56a, preferably two hooks 56a, on proximal end 38a of the shield adjacent elongate opening 44a and at least one lug 58a, preferably one lug 58a, on mount 52a. Hooks 56a and lug 58a are disposed to engage releasably. Lug 58a includes a deflectable projection 60a disposed so that when projection 60a is deflected toward the axis of assembly 10a, hooks 56a and lug 58a are disengaged and shield 36a is pivotable about hinge 50a to its open position.

Hinge 50a has two arms 62a projecting proximally from open end 38a of the shield opposite open slot 44a. Each arm 62a has a perpendicularly extending peg 64a, with mount 52a having two holes 66a therein sized and disposed to receive a peg 64a to form a pivotal hinge 50a and to attach shield 36a to mount 52a. Shield 36a is movable about the pivotal hinge 50a between the latched position the open position.

Mount 52a has an axial opening 68a therethrough that is sized and shaped to receive at least a portion of needle hub 22a. Preferably, opening 68a includes a groove 70 for receiving a projection 72 on the outside surface 28a of the needle hub to retain needle hub 22a in the mount while allowing an annular rotation of mount 52a about hub 22a as indicated by the arrow in FIG. 15. When hub 22a is positioned in opening 68a of the mount of mount 52, projection 72 engages groove 70, retains the hub in the mount and allows rotation of the mount with the shield about the hub. The ability to rotate the mount and the shield about the hub is important for procedures that are needle point orientation sensitive, such as phlebotomy. In performing a phlebotomy, a practitioner generally uses a needle 14a with a sharp distal point 18a having a beveled surface 19a. The practitioner positions the needle substantially parallel and at a shallow angle to the patient's skin above the target blood vessel with beveled surface 19a facing upwardly. If the shielded needle assembly only has a pivotal shield, unless the needle point bevel is oriented with respect to the pivot on the needle shield during assembly, in some applications, the needle shield may be an obstacle to the practitioner's placement of the needle in the patient's blood vessel. In the more preferred embodiment of the invention shown in FIGS. 15 and 16, mount 52a is rotatable about needle hub 22a, allowing the practitioner to position shield 36a in a radial orientation that does not interfere with the procedure. The ability to orient the needle shield about the hub allows the needle to be assembled into the hub without any restraint placed on orientation, allowing the assembly efficiency to be substantially equal to the efficiency of standard unshielded assemblies. Additionally, in this embodiment, it is preferred that mount 52a include a stop 74 to limit the rotation of hub 22a within mount 52a to less than one complete rotation to facilitate threading and unthreading for mounting and dismounting of needle assembly 10a on a fluid handling device.

Figure 17:
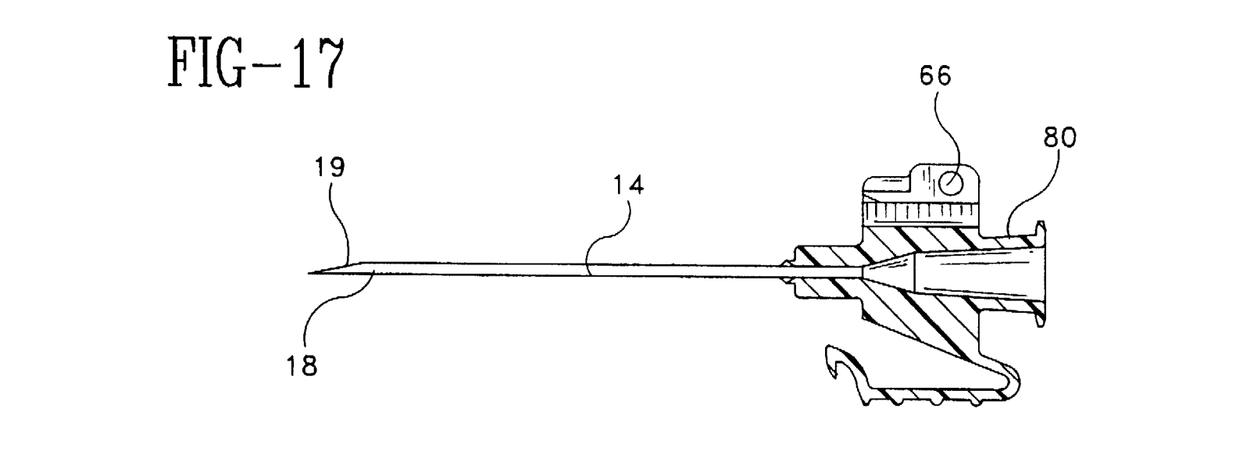
FIG. 17 is a partial cross-sectional view of another embodiment of the assembly of the present invention.

As an alternative for applications where needle point orientation is not important to the procedure or when the needle point bevel 19 is oriented during the manufacturing process, the hub and mount may be integrally formed as a unitary structure 80, as is illustrated in FIG. 17.

Figure 18:
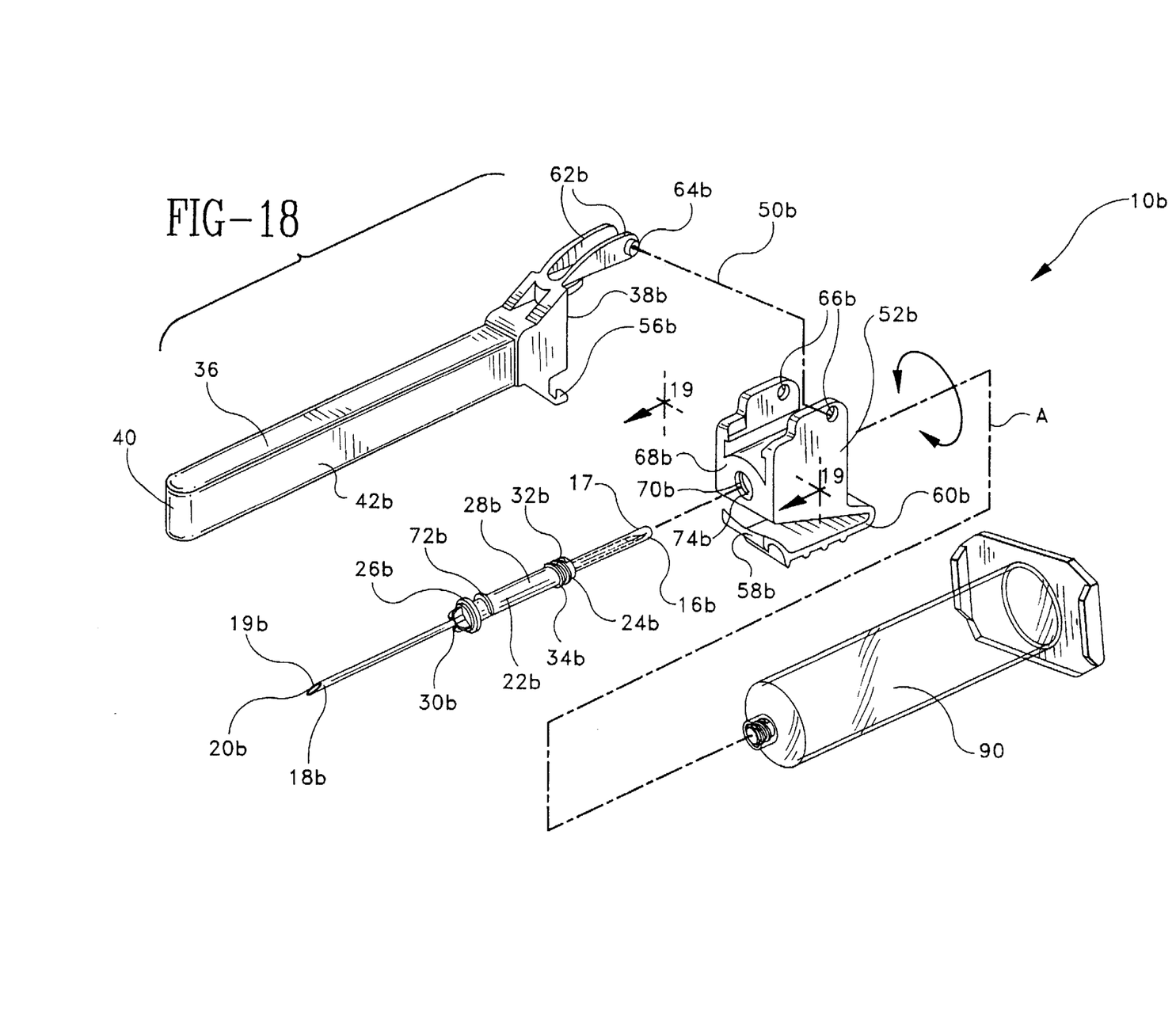
FIG. 18 is an exploded perspective view an embodiment of the assembly of the present invention wherein the needle assembly includes a two-ended phlebotomy needle for mounting in a phlebotomy needle holder.
Figure 19:
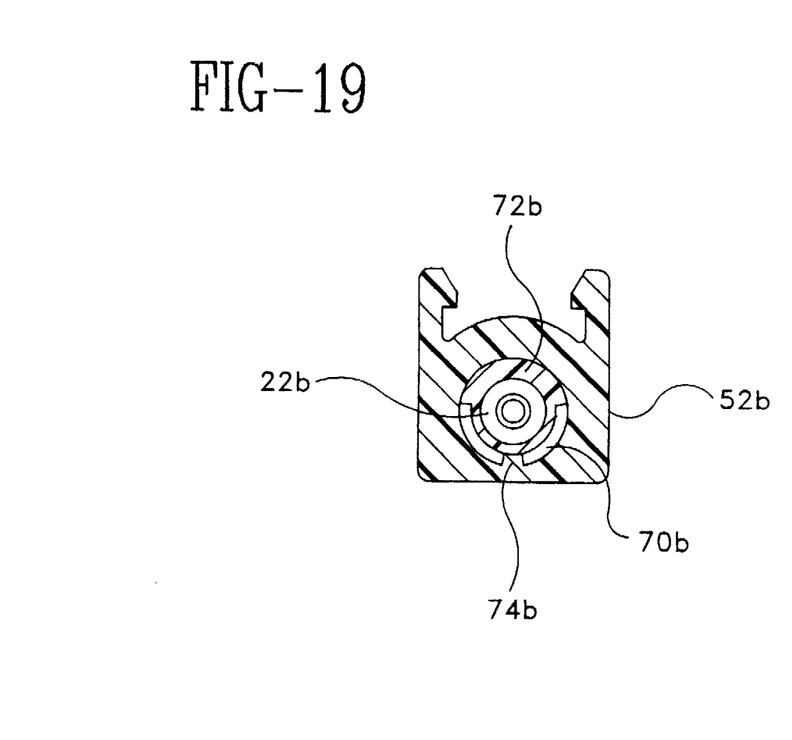
FIG. 19 is a cross-sectional view of the mount from FIG. 18 taken along the line 19—19.
Figure 19A:
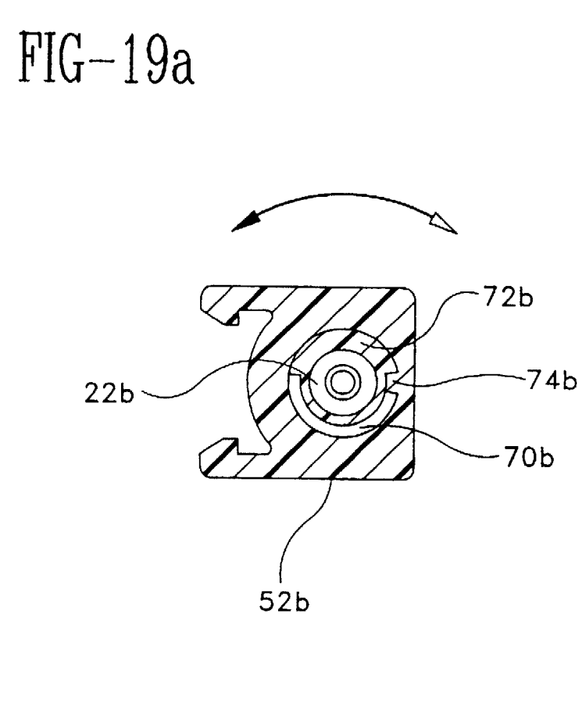
FIG. 19a is a cross-sectional view, analogous to FIG. 19, illustrating rotation of the mount with respect to the needle hub.

FIGS. 18, 19 and 19a illustrate another embodiment of the shielded needle assembly of the invention useful for a two-ended phlebotomy needle suitable for mounting on a needle holder. In this embodiment the structure of the needle assembly is also substantially similar to the assembly illustrated in FIGS. 1–14. Accordingly, substantially similar components that perform substantially similar functions are numbered identically to those components of the embodiment of FIGS. 1–14 except that a suffix "b" is used to identify those components in FIGS. 18, 19 and 19a. Needle assembly 10b of the present invention includes an elongate needle 14b with a sharp proximal end 16b that has a resilient closure valve 17, a sharp distal end 18b with a beveled surface 19b and a passageway 20b therethrough. Assembly 10b has a needle hub 22b with a proximal end 24b, a distal end 26b and an outside surface 28b. Hub 22b has an axial opening 30b therethrough to receive and hold needle 14b with end 16b of the needle projecting proximally and with distal end 18b of the needle projecting distally axially. Proximal end 24b of the needle hub further includes a fitting 32b for releasably mounting the needle hub on a fluid handling device, preferably, external threads 34b for use on needle holder 90. Assembly 10b further includes an elongate shield 36b with an open proximal end 38b, a distal, preferably closed, end 40b and a sidewall 42b that has an elongate opening 44b on one side 46b extending from distal end 40b to open end 38b. Shield 36b of the invention is movable between an open position in which needle 14b is exposed for use by passage through elongate opening 44b and a latched position in which shield 36b is substantially prevented from movement to the open position and shield 36b substantially obstructs access to needle 14b. Assembly 10b has a hinge 50b including a mount 52b for holding shield 36b onto needle hub 22b with shield 36b movable between the open position and the latched position by an off-axis pivotal movement about hinge 50b. There is a latch 54b for releasably latching shield 36b to mount 52b. Latch 54b includes at least one hook 56b, preferably two hooks 56b, on proximal end 38b of the shield adjacent elongate opening 44b and at least one lug 58b, preferably one lug 58b, on mount 52b. Hooks 56b and lug 58b are disposed to engage releasably. Lug 58b includes a deflectable projection 60b disposed so that when projection 60b is deflected toward the axis of assembly 10b, hooks 56b and lug 58b are disengaged and shield 36b is pivotable about hinge 50b to its open position.

Hinge 50b has two arms 62b projecting proximally from open end 38b of the shield opposite open slot 44b. Each arm 62b has a perpendicularly extending peg 64b, with mount 52b having two holes 66b therein each sized and disposed to receive a peg 64b to form a pivotal hinge 50b and to attach shield 36b to mount 52b. Shield 36b is movable about the pivotal hinge 50b between the latched position and the open position.

Mount 52b has an axial opening 68b therethrough that is sized and shaped to receive at least a portion of needle hub 22b. In this embodiment, opening 68b also includes provisions retaining needle hub 22b in the mount and allowing an annular rotation of mount 52b about hub 22b as indicated by the arrow in FIG. 18. Preferably, opening 68b includes a groove 70b for receiving a projection 72b on the outside surface 28b of the needle hub. When hub 22b is positioned in opening 68b of the mount of mount 52b, projection 72b engages groove 70b, retaining the hub in the mount and allowing rotation of the mount with the shield about the hub. The ability to rotate the mount and the shield about the hub is important for procedures that are needle point orientation sensitive, such as phlebotomy. In performing a phlebotomy, a practitioner generally uses a needle 14b with a sharp distal point 18b having a beveled surface 19b. The practitioner positions the needle substantially parallel and at a shallow angle to the patient's skin above the target blood vessel with bevel 19b facing upwardly. If the needle assembly has a pivotal shield, unless the needle point is oriented to the pivot on the needle shield during manufacture assembly, the needle shield may be an obstacle to the practitioner's placement of the needle in the patient's blood vessel. In the embodiment of the invention shown in FIGS. 18, 19 and 19a, mount 52b is rotatable about needle hub 22b, allowing the practitioner to position shield 36b in a radial orientation that does not interfere with the procedure. The ability to orient the needle shield about the hub allows the needle to be assembled into the hub without any restraint being placed on orientation, allowing the assembly efficiency to be substantially equal to the efficiency of standard unshielded assemblies. Additionally, in this embodiment, it is preferred that mount 52b include a stop 74b to limit the rotation of hub 22b within mount 52b to less than one complete rotation to facilitate threading and unthreading for mounting and dismounting needle assembly 10b into fluid handling devices, such as phlebotomy needle holder 90.

Suitable materials for forming the shield, needle hub and mount of the invention include, but are not limited to, thermoplastic polymeric resins such as polypropylene, polystyrene, polycarbonate, acrylonitrile/butadiene/styrene, and the like. Suitable materials for forming the needle of the assembly include stainless steels.

The needle assembly of the invention allows a practitioner to open and close the shield over the needle without placing his hands in close proximity to the distal point of the needle. The shielded needle assembly of the invention is particularly useful in clinical practice applications that require filling a syringe with a medication at a location remote from the location where the medication is administered to the patient. The syringe may be filled and the shield reclosed substantially without risk of damage to the needle that might be caused by a mis-replacement of a standard needle shield. Additionally, in the more preferred embodiment, the shielded assembly of the invention allows annular rotation of the shield with respect to the needle in addition to the pivotal opening and closure of the shield about the hub of the needle. The rotation of the shield about the hub enables a practitioner to position the shield to substantially eliminate interference of the shield with a procedure.

What is claimed is:

1. A needle assembly comprising:

an elongate needle having a proximal end, a distal end and a passageway therethrough;

a needle hub having a proximal end, a distal end and an exterior surface, said needle hub having an axial opening therethrough to receive and hold said needle at said distal end of said needle hub with said distal end of said needle projecting distally axially therefrom, said proximal end of said needle hub further including means for releasably mounting said needle hub on a fluid handling device;

an elongate shield having an open proximal end, a distal end and a sidewall having an elongate opening on one side;

hinge means including a mount for retaining said shield onto said needle hub, said mount sized and shaped to receive at least a portion of said needle hub;

said shield being movable about said hinge means by an off-axis pivotal movement between an open position, wherein said distal end of said needle is exposed, and a latched closed position, wherein said shield substantially obstructs access to said needle; and latch means for releasably latching said shield to said mount including at least one hook on said proximal end of said shield adjacent to said elongate opening and at least one lug on said mount, said hook and said lug being disposed to engage releasably when said shield is moved to said latched position, said lug including a deflectable projection disposed so that when said projection is deflected, said hook and said lug are disengaged and said shield is pivotable about said hinge means to said open position.

2. The needle assembly of claim 1 wherein said hinge means comprises two arms projecting proximally from said open end of said shield opposite said open slot, said arms each having a perpendicularly extending peg, and said mount having two holes therein sized and disposed to receive said pegs thereby forming a pivot and attaching said shield to said mount, said shield being movable with respect to said mount about said pivot.

3. The needle assembly of claim 1 wherein said latch means comprises said shield having two hooks, said hooks being adjacent said elongate slot and projecting proximally, wherein said lug extends outwardly on said projection, said lug being disposed to engage said hooks releasably when said shield is in said closed position and disengage said from said hooks when said projection is deflected.

4. The needle assembly of claim 1 wherein said means for releasably mounting said needle hub on the fluid handling device comprises a female luer fitting.

5. The needle assembly of claim 1 wherein said distal end of said shield is closed.

6. The needle assembly of claim 1 further including means for fixedly attaching said mount on said needle hub, said means for fixedly attaching being selected from the group consisting of an adhesive bond between said needle hub and said opening, a mechanical interference fit between said needle hub and said opening, a solvent bond between said needle hub and said opening, a thermal weld between said needle hub and said opening, and a mechanical snap-fit.

* * * * *